United States Patent [19]

Saito et al.

[11] 4,196,289

[45] Apr. 1, 1980

[54] PROCESS FOR PRODUCING TRIALLYL ISOCYANURATE

[75] Inventors: Hiroyasu Saito; Akio Sekiguchi, both of Iwaki, Japan

[73] Assignee: Nippon Kasei Chemical Co., Ltd., Iwaki, Japan

[21] Appl. No.: 940,117

[22] Filed: Sep. 6, 1978

[30] Foreign Application Priority Data

Mar. 31, 1978 [JP] Japan .................................. 53/37739

[51] Int. Cl.$^2$ ............................................ C07D 251/34
[52] U.S. Cl. .................................................... 544/221
[58] Field of Search ......................................... 544/221

[56] References Cited

U.S. PATENT DOCUMENTS

| 2,536,849 | 1/1951 | Kaiser et al. ........................ 544/221 |
| 3,037,979 | 6/1962 | Fukui et al. .......................... 260/248 |
| 4,056,547 | 11/1977 | Tanaka et al. ....................... 544/221 |

FOREIGN PATENT DOCUMENTS 2038526  2/1971  Fed. Rep. of Germany .

*Primary Examiner*—John M. Ford
*Attorney, Agent, or Firm*—Stevens, Davis, Miller & Mosher

[57] ABSTRACT

A process for producing tri(allyl isocyanurate) by reacting an alkali cyanate and an allyl halide in an aprotic polar solvent, which comprises distilling off the solvent after the completion of the reaction, adding water or an aqueous solution of hydrogen chloride to a reaction mixture containing tri(allyl isocyanurate), forming a tri(allyl isocyanurate) layer and an aqueous layer and then separating the tri(allyl isocyanurate) layer from the aqueous layer.

7 Claims, No Drawings

PROCESS FOR PRODUCING TRIALLYL ISOCYANURATE

This invention concerns an improved process for producing a tri(allyl isocyanurate) by reacting an allyl halide and an alkali cyanate.

Tri(allyl isocyanurate) is useful as starting material or as an intermediate in the production of synthetic resins, including synthetic rubber and other organic chemicals.

A process for producing a tri(allyl isocyanurate) by reacting an alkali cyanate and an allyl halide in an aprotic polar solvent is disclosed in Japanese Patent Publication No. 3985/1961, which process forms a slurry after the completion of the reaction due to the salts produced as by-products. For the recovery of tri(allyl isocyanurate) as the reaction product, various salt removing methods have been employed such as suction filtration, pressure filtration, centrifugal separation and the like. But these salt removing methods result in a great loss in the reaction products and the solvent since the reaction products and the solvent deposited an the salts are removed together. Avoidance of such loss requires washing of the salts with a solvent, recovery of the solvent attached to the salts and the like, which often results in industrial disadvantages. Another known process for the removal of the salts is a water-washing process in which the salts are dissolved by the direct addition of water to the slurry after the completion of the reaction. But this process also results in a great loss in the reaction products dissolved into the water-solvent system and causes difficulty in the separation of the aqueous layer from the reaction products, requiring the use of an additional extraction solvent. The filtration of the slurry after the completion of the reaction requires an aprotic polar solvent for the washing of the filtered cake (salts) and since this solvent dissolves the salts considerably, the salts which are deposited upon recovery of the solvent have to be removed again. Mere fractional distillation of the slurry after the completion of the reaction upon purification of tri(allyl isocyanurate) is difficult since 1,3-diallylurea, diallylcarbonate, allyl N-allylcarbamate and the like, produced as by-products in the reaction, are incorporated in the tri(allyl isocyanurate) fraction.

As described above, the conventional processes for producing tri(allyl isocyanurate) are disadvantageous in that the reaction products and the solvent cannot easily be separated and recovered from the reaction system after the completion of the reaction.

This invention provides a process for producing a tri(allyl isocyanurate) by reacting an alkali cyanate and an allyl halide in an aprotic polar solvent, distilling to remove the solvent from the solution after the completion of the reaction, adding water or an aqueous solution of hydrogen chloride to the resulting reaction mixture containing tri(allyl isocyanurate) thus forming a tri(allyl isocyanurate) layer and an aqueous layer and then separating the tri(allyl isocyanurate) layer from the aqueous layer.

In the process for producing tri(allyl isocyanurate) by reacting an allyl halide and an alkali cyanate in an aprotic solvent, it is assumed that allyl isocyanate is formed at first as an intermediate product as shown in the following reactions (1) and (2) and then the allyl isocyanate is trimerized (polymerization) in the same reaction system to form an tri(allyl isocyanurate):

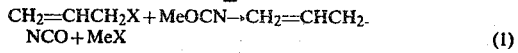

$$CH_2=CHCH_2X + MeOCN \rightarrow CH_2=CHCH_2NCO + MeX \quad (1)$$

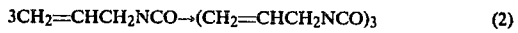

$$3CH_2=CHCH_2NCO \rightarrow (CH_2=CHCH_2NCO)_3 \quad (2)$$

If water is present in the reaction system in the above reaction, it results in the side reactions as shown in reaction formulas (3), (4) and (5) to reduce the tri(allyl isocyanurate) yield significantly.

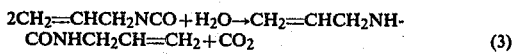

$$2CH_2=CHCH_2NCO + H_2O \rightarrow CH_2=CHCH_2NHCONHCH_2CH=CH_2 + CO_2 \quad (3)$$

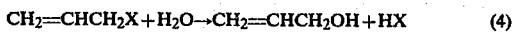

$$CH_2=CHCH_2X + H_2O \rightarrow CH_2=CHCH_2OH + HX \quad (4)$$

$$CH_2=CHCH_2NCO + CH_2=CHCH_2OH \rightarrow CH_2=CHCH_2NHCOOCH_2CH=CH_2 \quad (5)$$

(where X represents a halogen and Me represents an alkali metal). The water content in the reaction system greatly hinders the formation of the tri(allyl isocyanurate), for example, by the hydrolysis of the aprotic polar compound as the solvent in addition to the above side reactions (3), (4) and (5). Inclusion of water in the reaction system should therefore be avoided as much as possible. The aprotic polar compound used for the reaction solvent and the alkali cyanate used as the starting materials for the reaction are, however, highly hygroscopic and their industrial grades contain much water.

Such water content deleterious to the reaction, can be removed by charging the hygroscopic solvent and alkali cyanate in a reactor prior to the reaction of allyl halide and alkali cyanate and dehydrating them through distillation. After the dehydrating distillation, allyl halide is charged into the reactor and the reaction can be carried out for the formation of tri(allyl isocyanurate) while suppressing the above undesired side-reactions and the hydrolysis of the solvent.

The foregoing dehydrating distillation can be effected by charging the above solvent and the alkali cyanate into the reactor and then partially distilling the solvent under atmospheric or reduced pressure to thereby remove the water together with the solvent, or by adding an organic solvent such as benzene, toluene or xylene that is inert to the reaction solvent, starting materials for the reaction and the intermediate products in the reaction, and capable of forming an azeotropic compound with water to thereby remove water contained in the reaction solvent and in the alkali cyanate through azeotropic distillation.

In the tri(allyl isocyanurate) forming reaction, it is undesirable to introduce the allyl halide at once or dropwise onto the surface of the reaction zone in the reactor. This is attributable to the fact that since the allyl halide has a boiling point (most allyl halides boil below 103° C.) lower than the reaction temperature (above about 110° C.), allyl halide, either charged directly as the starting material or circulated by way of reflux to the reaction zone, is evaporated at its surface. This greatly lowers the concentration of allyl halide in the reaction zone and thus requires a reflux condenser of a great capacity, as well as repeated reflux over a long period of time. However, prolonging the reaction causes the hydrolysis of the allyl halide and accompanying side reactions.

While another method of effecting the reaction under pressure is also known for increasing the concentration of the allyl halide in the reaction zone, this results in an increase in the resinous by-products to reduce the yield of tri(allyl isocyanurate) as the end product, although the reason therefor is not clear.

In conducting the reaction, direct introduction of the allyl halide to the liquid phase in the reaction zone is advantageous in order to increase the concentration of the allyl halide in the liquid phase in the reaction zone and produce tri(allyl isocyanurate) at a good yield in a short time.

The allyl halide introduction can be effected by premixing the alkaly cyanate in the aprotic polar solvent, increasing the temperature of the resultant mixture to reaction temperature, and then introducing allyl halide through a suitable conduit pipe in communication with the reaction mixture liquid phase or through an inlet provided on the side wall of the reaction vessel, below the surface of the liquid phase. Allyl halide evaporated during reaction is cooled and condensed by a reflux condenser and then introduced again through the above conduit pipe or vessel side inlet. Any type of conduit pipe or vessel inlet may be used so long as it permits direct introduction of liquid or gaseous allyl halide into the reaction zone.

Allyl halide can be introduced by any method such as by way of the head pressure of the ally halide, by introduction of the allyl halide together with an inert gas, for example, nitrogen, by pumping and the like.

The direct introduction of the starting allyl halide or refluxed allyl halide into the liquid phase of the reaction zone provides advantageous results such as much shortened reaction time, increased tri(allyl isocyanurate) yield and significant control for the occurrence of the side reactions, as compared with the prior method in which the allyl halide is added dropwise to the surface of the liquid phase of the reaction mixture.

The distillation of the solvent from the reaction solution for the satisfactory fractional recovery of the reaction products and the solvent in the process according to this invention, after the completion of the tri(allyl isocyanurate) forming reaction, may be carried out either under atmospheric or a reduced pressure, but an adequate consideration should be made for the stirring power and the like since the system is in the form of a slurry and its viscosity is increased by the distillation process.

Formation of the tri(allyl isocyanurate) layer and the aqueous layer requires a temperature at which tri(allyl isocyanurate) will melt into a solution form. The temperature may be relatively low where a great amount of the aprotic polar solvent remains to be eliminated from the reaction solution slurry but should be relatively high where the remaining amount of the solvent is small. The temperature is above about 15° C., preferably, above 20° C. and, more preferably, above 30° C. in general practice. The amount of the water or the aqueous hydrochloride solution for forming the aqueous layer is such that it is sufficient to dissolve the salts formed upon reaction.

Where much alkali carbonate is contained in the starting alkali cyanate, it is known to use the salt of a metal belonging to group II in the periodic table (Japanese Patent Publication No. 26766/1967). Since the carbonate of the group II metal remains in addition to the foregoing salts, the use of the aqueous hydrogen chloride solution is effective for its dissolution in such a case. While the salt solution dissolved in water is basic and that in the aqueous hydrogen chloride solution is acidic, the tri(allyl isocyanurate) reaction product is stable under both basic and acidic conditions.

The temperature of the water or the aqueous hydrogen chloride solution used in the process of this invention may be controlled to avoid crystallizing out tri(allyl isocyanurate) and is, preferably, above 23° C., more preferably, above 30° C. and up to boiling temperature, a higher temperature being effective where the by-products are to be dissolved out. A sufficient amount of the water or the aqueous hydrogen chloride solution used as is required for dissolving the salts. The number of washing cycles is not restricted.

The aprotic polar solvents used in this invention include, for example, dimethylformamide, dimethylsulfoxide, N-methylacetamide, acetonitrile, tetramethylurea and the like. The alkali cyanates include those compounds represented by the chemical formulas MeOCN or MeNCO (where Me represents an alkali metal). Representative compounds are lithium cyanate, potassium cyanate and sodium cyanate, alone or in admixture. The allyl halides include allyl bromide, allyl chloride, allyl iodide and the like.

The tri(allyl isocyanurate) layer obtained in this invention has a high purity that can be used as a final product as such but it can be further purified by, for example, distillation under reduced pressure into a tri(allyl isocyanurate) of high purity.

This invention is further described by the following examples, in which % means % by weight.

EXAMPLE 1

Into a 500-liter reactor, 150 kg of dimethylformamide, 80 kg of sodium cyanate, containing 5% by weight of sodium carbonate as an impurity, and 1 kg of potassium bromide were introduced, and then, while heating the content to 130° C. with agitation, 76.5 kg of allyl chloride were added to the mixture in the reactor over a period of 3 hours. After agitating the mixture for 3 hours at 130°–135° C., dimethylformamide was distilled off under reduced pressure and was recovered. Then, 250 liters of water were added to the distillation residue and it was heated to 40° C. and agitated for 30 minutes. The aqueous layer which separated after leaving the reactant to stand still was removed, and the layer containing tri(allyl isocyanurate) was washed two times, each washing being with 100 liters of water at 30° C. After separation from the water layer, the layer of tri(allyl isocyanurate) was dehydrated by heating and distilled at 113°–115° C./1 mm Hg.

EXAMPLE 2

In a reactor as in Example 1, 150 kg of dimethylformamide, 85 kg of sodium cyanate containing 10% by weight of sodium carbonate, 5 kg of anhydrous calcium chloride and 1 kg of potassium bromide were introduced and the contents of the reactor were made to react as in Example 1, then dimethylformamide was recovered. Two hundred and fifty liters of water at 30° C. were added to the reactant and then a volume of concentrated hydrochloric acid was slowly added to it with agitation to adjust the pH of the water layer of 4.0. After leaving the reactant to stand still, the aqueous layer was removed and the layer of tri(allyl isocyanurate) was washed two times, each washing being with 100 liters of water at 30° C. After the second washing, neutralization was effected so that the pH of the aqueous layer became 7 by adding 1 N aqueous sodium hydroxide solution. The aqueous layer was removed and the layer of tri(allyl isocyanurate) was subjected to distillation as in Example 1 to obtain tri(allyl isocyanurate).

Comparative Example 1

The reactant obtained as in Example 1 cooled to room temperature was transferred to a 3 m³ container and 2,500 liters of water at 40° C. were added without distilling off dimethylformamide and the mixture was agitated. After leaving the mixture to stand still, because of the difficulty of liquid-separation, 200 liters of toluene were added to the mixture as an extractant, and the mixture was agitated and then left to stand still to recover the aqueous layer from which dimethylformamide was recovered by distillation. After distilling toluene from the toluene layer there was obtained tri(allyl isocyanurate) by distillation. The results are shown in Table 1 with those of Examples 1 and 2 as well as those of Comparative Example 2.

Comparative Example 2

The reactant obtained as in Example 2 cooled to room temperature was subjected to centrifugation to remove solid salts and then dimethylformamide was recovered by distillation of the separated liquid. Simultaneously with the distillation of dimethylformamide, salts which had dissolved in the liquid reappeared to convert the liquid to a viscous slurry which made the removal of the salts by filtration difficult. Then, 100 liters of toluene were added to the slurry to dilute it, and after filtration under pressure of the diluted slurry, toluene was distilled off to obtain tri(allyl isocyanurate).

Table 1

| Example | % Recovery dimethylformamide | Yield (%)* of tri(allyl isocyanurate) | Purity (%)** tri(allyl isocyanurate) |
|---|---|---|---|
| Example 1 | 98.5 | 92.0 | 99.1 |
| Example 2 | 98.0 | 93.3 | 99.3 |
| Com. Ex. 1 | 72.3 | 91.5 | 97.8 |
| Com. Ex. 2 | 87.1 | 83.0 | 97.2 |

Notes:
*Yield based on allyl chloride.
**Purity found by Gaschromatography.

EXAMPLE 3

To a 20 l reactor equipped with a stirrer, a thermometer, an allylhalide feed pipe terminating in the bottom of the reactor, a condenser having a reflux liquid conduit extending to the bottom of the reactor, and fitted with a 10-stage rectifier column, were charged 4,300 g dimethylformamide with 0.1% water content, 2,000 g sodium cyanate of 92% purity and 0.2% water content, 75 g anhydrous potassium chloride, and 7 g potassium bromide. After closing the allyl halide feed pipe and the reflux solution conduit, the contents were heated to about 90° C. with stirring and 450 g formamide was distilled off under a reduced pressure of 95–100 mm Hg and with a reflux ratio of 5.0. The water remaining in the system was 0.03%. Then, the temperature inside of the reactor was increased to 130° C. and 2,080 g allyl chloride was added by its head pressure over three hours through the allyl halide feed pipe, with the allyl halide conduit pipe and the reflux solution conduit being open and the rectifier entrance being closed, respectively. Then, the allyl halide conduit pipe was closed and the reaction solution was maintained at 130°–135° C. for two hours while stirring. After that, the reaction solution was cooled to 60° C. and dimethylformamide was distilled off under a reduced pressure of 25 mmHg and taken out of the system for recovery through the side pipe of the reflux solution conduit.

9500 l water and 550 g 35% aqueous hydrogen chloride solution were added to a mixture of the residual crude tri(allyl isocyanurate) and inorganic salts, stirred to completely dissolve out the inorganic salts and allowed to stand still, and then the separated lower aqueous layer was discharged. 5000 l water was added to the remaining crude tri(allyl isocyanurate), stirred and allowed to stand still. Then, the lower layer of the crude tri(allyl isocyanurate) was transferred to the distiller, dehydrated under vacuum below 100° C. and then distilled under 113° C./0.5 mmHg to obtain 2016.5 g tri(allyl isocyanurate).

What is claimed is:

1. In a process for producing triallyl isocyanurate by reaction of an alkali cyanate and an allyl halide in the presence of an aprotic polar solvent, to form a reaction mixture comprising the triallyl isocyanurate, the aprotic polar solvent and salt by-product, the improvement comprising:
    distilling said reaction mixture to remove said aprotic polar solvent;
    adding water or an aqueous solution of hydrogen chloride to the distilled reaction mixture thereby forming a triallyl isocyanurate layer and an aqueous layer; and
    separating the triallyl isocyanurate layer from said aqueous layer.

2. The process of claim 1, in which the reaction is effected in the presence of a salt of group II metal of the periodic table and wherein the tri(allyl isocyanurate) layer and the aqueous layer are formed by the addition of an aqueous solution of hydrogen chloride.

3. The process of claim 1, in which said solvent removal is by distillation under reduced pressure.

4. The process of claim 1 wherein water introduced within the solvent and alkali cyanate is first removed, and then the allyl halide is added to form said reaction mixture.

5. The process of claim 4 wherein said water removal is by distillation.

6. The process of claim 5 in which a solvent which forms an azeotrope with water, but which is inert to the aprotic polar solvent, is added prior to distillation and the resulting azeotropic mixture of solvent and water is removed by the distillation.

7. The process of claim 1 wherein the allyl halide is introduced into the liquid phase of the reaction mixture through a conduit in direct communication with the liquid phase.

* * * * *